United States Patent [19]

Farnham

[11] Patent Number: 5,268,511
[45] Date of Patent: Dec. 7, 1993

[54] PRODUCTION OF TRIFLUORVINYL ETHERS

[75] Inventor: William B. Farnham, Hockessin, Del.

[73] Assignee: E. I. Du Pont de Nemours and Company, Wilmington, Del.

[21] Appl. No.: 859,181

[22] Filed: Mar. 27, 1992

[51] Int. Cl.$^5$ .................. C07C 41/24; C07C 315/04; C07C 69/65
[52] U.S. Cl. ........................ 568/685; 568/684; 568/615; 568/674; 568/32; 562/825; 560/183; 560/129; 558/51; 558/381; 558/449; 556/450; 556/456; 556/460; 556/467
[58] Field of Search ............... 568/615, 32, 685, 674; 562/825, 887; 560/183, 184, 129; 558/381, 51, 449; 556/450, 456, 460, 467

[56] References Cited

PUBLICATIONS

J. D. Citron, *J. Organometal. Chem.*, vol. 30, pp. 21–26 (1971).

*Primary Examiner*—Marianne M. Cintins
*Assistant Examiner*—Margaret J. Page

[57] ABSTRACT

A two step process, each of the steps being novel, for the production of trifluorovinyl ethers by reaction of a siloxane with selected acyl fluorides or carboxylic anhydrides, is disclosed. Also disclosed is a novel silyl ester intermediate.

22 Claims, No Drawings

PRODUCTION OF TRIFLUORVINYL ETHERS

FIELD OF THE INVENTION

Disclosed herein is a novel process for making trifluorovinyl ethers by reacting selected acyl fluorides or anhydrides with siloxanes, and then thermolyzing the resulting silyl ester to form the trifluorovinyl ether and a fluorosilane. The fluorosilane may be recycled to siloxane.

TECHNICAL BACKGROUND

Trifluorovinyl ethers are used commercially as comonomers in polymers, particularly as comonomers in highly fluorinated polymers which are often chemically and/or thermally relatively stable. The ethers are usually made by the gas or liquid phase thermolysis of the corresponding acyl fluoride over a bed of reactant and/or promoter. However, these reactions often give only fair yields of the trifluorovinyl ether and tend to generate relatively large amounts of toxic waste, which are difficult and expensive to dispose of. In the novel process described herein, particularly when run under the preferred conditions, good yields of the desired trifluorovinyl ether are obtained, and little toxic waste is generated, as most of the byproducts can be recycled in the process, and/or are otherwise useful.

J. D. Citron, J. Organometal. Chem., vol. 30, p. 21-26 (1971) reported (in Table 1 therein) that siloxanes reacted with acyl fluorides to form carboxyl anhydrides and fluorosilanes.

SUMMARY OF THE INVENTION

This invention concerns a process for the production of trifluorovinyl ethers, comprising:
a) reacting a compound containing the group —O(C$_2$F$_4$)COF or the group —O(C$_2$F$_4$)C(O)O(O)C(C$_2$F$_4$)O— with a siloxane;
b) heating the silyl ester in the presence of a thermolysis catalyst, at a temperature of about 140° C. to about 350° C. to produce a trifluorovinyl ether and a fluorosilane; provided that where b) is carried out in the gas phase, said thermolysis catalyst is not a diaryl sulfone.

This invention includes a process for the production of silyl esters, comprising, reacting a compound of the formula R$^1$[O(C$_2$F$_4$)COF]$_z$ or a compound of the formula R$^1$[O(C$_2$F$_4$)C(O)O(O)C(C$_2$F$_4$)O]$_z$R$^1$ with a siloxane, to form a silyl ester, and wherein:
R$^1$ is a hydrocarbyl or substituted hydrocarbyl radical having z free valencies; and
z is 1 or 2.

This invention also concerns a process for the production of a trifluorovinyl ether, comprising, heating a silyl ester of the formula R$^1$[O(C$_2$F$_4$)C(O)OSiR$^2$$_3$]$_z$, in the presence of a thermolysis catalyst, at a temperature of about 140° C. to about 350° C., to produce a trifluorovinyl ether and a fluorosilane, and wherein;
R$^1$ is a hydrocarbyl or substituted hydrocarbyl radical having z free valencies;
each R$^2$ is independently hydrocarbyl, substituted hydrocarbyl or an oxysilyl group; and
z is 1 or 2;
provided that when carried out in the gas phase said thermolysis catalyst is not a diaryl sulfone.

This invention also includes a silyl ester of the formula R$^1$[O(C$_2$F$_4$)C(O)OSiR$^3$$_3$]$_z$, wherein:

R$^1$ is a hydrocarbyl or substituted hydrocarbyl radical having z free valencies;
each R$^3$ is independently hydrocarbyl, substituted hydrocarbyl, or oxysilyl; and
z is 1 or 2.

DETAILS OF THE INVENTION

This invention deals with a process for producing trifluorovinyl ethers from selected acyl fluorides or carboxylic anhydrides. The process involves two steps, each of which is novel, and a novel intermediate is involved. The chemical reactions are believed to be:

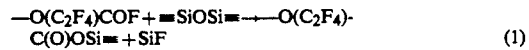
$$\text{—O(C}_2\text{F}_4\text{)COF} + \equiv\text{SiOSi}\equiv \longrightarrow \text{—O(C}_2\text{F}_4\text{)C(O)OSi}\equiv + \text{SiF} \quad (1)$$

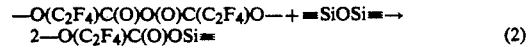
$$\text{—O(C}_2\text{F}_4\text{)C(O)O(O)C(C}_2\text{F}_4\text{)O—} + \equiv\text{SiOSi}\equiv \longrightarrow 2\text{—O(C}_2\text{F}_4\text{)C(O)OSi}\equiv \quad (2)$$

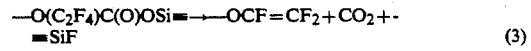
$$\text{—O(C}_2\text{F}_4\text{)C(O)OSi}\equiv \longrightarrow \text{—OCF=CF}_2 + \text{CO}_2 + \equiv\text{SiF} \quad (3)$$

Reaction conditions and catalysts are not shown in these equations, and in the complete process, either reaction (1) or reaction (2) would be done, followed by reaction (3). In these equations, only the "essential" parts of the reactants are shown. By "essential" is meant those parts of the reacting compounds that undergo chemical change during the process.

The (parts of) the compounds that become the trifluorovinyl ether are —O(C$_2$F$_4$)COF and —O(C$_2$F$_4$)C(O)O(O)C(C$_2$F$_4$)O— when an acyl fluoride or a carboxylic anhydride are used, respectively. By the grouping "(C$_2$F$_4$)" is meant —CF$_2$CF$_2$— or —CF(CF$_3$)—. The grouping —CF(CF$_3$)— is preferred. The open bonds on the one or two (in the acyl fluoride and anhydride respectively) oxygen atoms are to hydrocarbyl or substituted hydrocarbyl groups. In addition, the acyl fluoride may have one or two of the essential groups shown above, and the anhydride may have one or two anhydride groups. Thus, using either of these starting materials, trifluorovinyl ethers having one or two trifluorovinyl ether groups can be obtained. In the case of an anhydride which has two anhydride groups, the representation above is a "formal" one, as it is possible that the anhydride may be polymeric, oligomeric or cyclic.

The following discussion of "R$^1$" is applicable not only to the immediately preceding compounds, but to all groups labeled "R$^1$" herein. The group attached to the free valence of the oxygen above may be designated as R$^1$. Thus the acyl fluoride that is used can be R$^1$[O(C$_2$F$_4$)COF]$_z$ where z is 1 or 2 and R$^1$ is a hydrocarbyl or substituted hydrocarbyl radical. By "hydrocarbyl" is meant a monovalent or divalent group containing only carbon and hydrogen. By "substituted hydrocarbyl"0 is meant a monovalent or divalent group containing only carbon and hydrogen which contains inert substituents. By "inert" in this context is meant that they do not change or react chemically during the process. The term "radical" herein means a group which does not change chemically during a chemical reaction or process. Suitable substituents when R$^1$ is substituted hydrocarbyl include, but are not limited to, fluorine, ether [between (substituted) hydrocarbyl segments], ester, sulfonyl fluoride, chloro, bromo, nitrile, sulfone [between (substituted) hydrocarbyl segments], sulfonate ester, and iodo. In one preferred embodiment all of the hydrogen atoms in R$^1$ are replaced by fluorine atoms. In another preferred embodiment all of the hydrogen atoms in $R^1$ are replaced by fluorine atoms, and $R^1$ is substituted with one or more of ether, ester, or sulfonyl fluoride. In another preferred embodiment $R^1$ is perfluoroalkyl, pentafluorophenyl, or perfluoroalkylene. In another preferred embodiment $R^1$ is perfluoroalkyl or perfluoroalkylene substituted with one or more of ether, ester, or sulfonyl fluoride. Particularly preferred $R^1$ groups are perfluoro-n-alkyl containing 1 to 12 carbon atoms, $-[CF_2CF(CF_3)O]_n(CF_2)_mCO_2CH_3$, and $-[CF_2CF(CF_3)]_tO(CF_2)_mSO_2F$ wherein n is 0 or an integer of 1 to 5, t is an integer of 1 to 5 and m is 2 or 3. The starting acyl fluorides can be made by known methods. See for example H. F. Mark, et al., Ed., Encyclopedia of Chemical Technology, 3rd Ed., John Wiley & Sons, New York, 1980, Vol. 10, p. 961 and W. Gerhartz, et al., Ed., Ullmanns Encyclopedia of Industrial Chemistry, 5th Ed., VCH, Weinheim, 1988, Vol. All, p. 366-367. The starting carboxylic anhydrides can be made from the acyl fluorides (see below) if desired.

Another of the needed ingredients for the process is a "siloxane". A siloxane is a compound that contains the grouping SiOSi with each of the free bonds to silicon bound to a hydrocarbyl, substituted hydrocarbyl, or oxysilyl group. By an oxysilyl group is meant the $-OSi\equiv$ group in which the free valencies of the silicon can be bound to a hydrocarbyl, substituted hydrocarbyl or additional oxysilyl groups. In this way, siloxanes containing many individual siloxane groups are built up. However, the only groups ever bound to any silicon atom (with the exception of end groups in polymers) in the siloxanes used herein, are hydrocarbyl, substituted hydrocarbyl and oxysilyl. Thus, siloxanes can contain either one siloxane group, as in hexamethyldisiloxane, can be cyclic compounds and contain several siloxane groups, as in octamethylcyclotetrasiloxane, or can contain many siloxane groups as in poly(dimethylsiloxane). Useful siloxanes, include, but are not limited to, hexamethyldisiloxane, 1,3-diphenyl-1,1,3,3-tetramethyldisiloxane, hexaethyldisiloxane, 1,3-diethyl-1,1,3,3-tetramethyldisiloxane, hexamethylcyclotrisiloxane, octamethylcyclotetrasiloxane, 1,3,5-triphenyl-1,3,5-trimethylcyclotrisiloxane, poly(dimethylsiloxane), poly(methyl-3,3,3-trifluoropropylsiloxane), and mixed cyclics and polymers such as poly(dimethylsiloxane-co-phenylmethylsiloxane). Preferred siloxanes are hexamethyldisiloxane, hexamethylcyclotrisiloxane, octamethylcyclotetrasiloxane, and 1,3-diethyl-1,1,3,3-tetramethyldisiloxane, and poly(dimethylsiloxane). A more preferred siloxane is hexamethyldisiloxane.

Many siloxanes are commercially available. A short review of siloxanes is found in V. Bazant, et al., Organosilicon Compounds, vol. 1, Academic Press, New York, 1965, p. 45-51, and references therein and T. C. Kendrick, et al., in S. Patai, et al., Ed., The Chemistry of Organic Silicon Compounds, John Wiley & Sons, New York, 1989, Chap. 21.

In the silyl esters used and claimed herein, it is preferred if each $R^2$ and $R^3$ is independently hydrocarbyl, more preferred if each $R^2$ and $R^3$ is independently phenyl or alkyl containing 1 to 4 carbon atoms, and most preferred if each $R^2$ and $R^3$ is independently methyl or ethyl.

The optional catalysts for reactions (1) and (2) are compounds that are sources of the carboxylate anion $-O(C_2F_4)CO_2^-$. It is preferred if the optional catalyst is present in reaction (1) and (2). The carboxylate anion itself (added as a salt) is such a source. Other sources (which in the process can form the carboxylate anion) include but are not limited to, silanolates, fluoride, and carboxylates such as acetate and perfluorooctanoate. In the process it is believed these compounds react with the acyl fluoride or carboxylic anhydride to form the carboxylate catalyst. It is preferred if the counterion to the carboxylate catalyst is an alkali metal cation. Thus, it is preferred if all of the above catalyst precursors are added as their alkali metal salts. Preferred catalyst precursors (sources of catalyst) are potassium silanolates and potassium perfluorocarboxylates.

Although not critical, it has been found useful to add 0.05 to 5 mole percent catalyst, based on equivalents of acyl fluoride present. Typically it is preferred if about 1 to 2 mole percent of the catalyst or source of catalyst is used.

The thermolysis catalyst herein is an aprotic compound capable of desilylating a silyl ester of the formula $-O(C_2F_4)CO_2Si\equiv$, or a diaryl sulfone. By an aprotic compound is meant a compound that does not contain active hydrogen, such as an alcohol, phenol, carboxylic acid, and primary and secondary amine. By capable of desilylating a silyl ester is meant that the compound causes the silicon atom to be removed from the oxygen atom of at least some of the silyl ester. This can occur through a simple chemical reaction in which the silyl ester is converted to another compound not having the Si—O— bond. It also includes compounds that may cause a rapid reaction to occur in which the silicon atoms of the silyl ester molecules rapidly equilibrate with one another (i.e., the silicon atoms in effect rapidly "move" from one carboxyl group to another). This is illustrated in Experiment 1.

Compounds capable of desilylating silyl esters (and are therefore thermolysis catalysts) include, but are not limited to, compounds which are a source of fluoride ion, perfluorocarboxylate salts (such as $-O(C_2F_4)CO_2^-$, but other perfluorocarboxylates are also effective), alkoxides, carboxylates, carbonates, and silanolates. In general, oxyanions and anions of carbon and sulfur acids whose conjugate acids have a pKa of about 2 to about 32 when measured in dimethylsulfoxide (see F. G. Bordwell, Accts. Chem. Res., Vol. 21, p. 456 (1988) on how such measurements are made and for a list of pKas) are effective desilylation compounds. It is believed that the desilylation reactions are nucleophilic attacks on silicon, which have been reviewed, see, for example, A. R. Bassindale, et al., in S. Patai, et al., Ed., The Chemistry of Organic Silicon Compounds, John Wiley & Sons, New York, 1989, Chap. 13. Preferred thermolysis catalysts are sources of fluoride ion, fluorinated carboxylate salts, and silanolates. Especially preferred thermolysis catalysts are sources of fluoride ion, particularly an alkali metal fluoride, and most preferred is potassium fluoride.

By a diaryl sulfone is meant a compound of the formula Ar—SO$_2$—Ar, where each Ar is independently an aryl or substituted aryl group. A preferred diaryl sulfone is diphenyl sulfone. A diaryl sulfone is not used as a thermolysis catalyst when the thermolysis is done in the gas phase.

Although not critical, it has been found useful to add 1 to 5 mole percent of the catalyst or catalyst precursor based on silyl ester, when reaction (3) is carried out in the liquid phase. When the reaction is carried out in the gas phase, it is preferred to have a relatively large surface area of fluoride catalyst over which the vapor will pass.

When reaction (3) is done in the liquid phase, it is preferred to have a cocatalyst present to facilitate reaction at a lower temperature. The cocatalyst is an organic compound which is capable of complexing with the cation of the fluoride ion source, for example the potassium ion of KF. Suitable compounds include, but are not limited to, crown ethers, linear polyethers, sulfones, and dialkyl pyrimidones. Although not critical, it has been found convenient to use 0.1 to 5 times the concentration of the thermolysis catalyst, of the cocatalyst.

For reaction (1) the process temperature is not critical, but it has been found convenient to use a temperature of 25° C. to 175° C., preferably 40° C. to 125° C. Although solvents could be used in this reaction, if desired, there is no need to do so, and it is preferred not to use solvents to avoid having to separate a solvent and product after the reaction. Reaction times typically range from about 0.5 to 24 hr., usually about to 5 hr. The reactants may optionally be agitated.

If desired the product silyl ester of reaction (1) may be isolated by distillation (assuming it has a low enough molecular weight), but the temperature in the distillation should be kept low enough to avoid reaction (3). By a silyl ester herein is meant a compound containing the grouping —$CO_2Si\equiv$, and which, for example, is believed made in reactions (1) and (2), and is the starting material for reaction (3). The esters made by (1) and (2) are novel, and are useful as intermediates for the production of trifluorovinyl ethers (as in reaction (3)).

The ratio of reactants in (1), that is siloxane groups to acyl fluoride groups, is not critical, but it is usually preferable to have an excess of siloxane groups, since this ensures complete reaction of the acyl fluoride and/or anhydride and simplifies isolation of the silyl ester product. When using a compound containing one siloxane group ($\equiv SiOSi\equiv$), it is preferred if the ratio of siloxane to acyl fluoride is 4:1 to 1:1, more preferably 1.25:1 to 1.01:1. When there is more than one siloxane group in the siloxane compound, it is preferred if the ratio of siloxane groups to acyl fluoride groups is 5:1 to 1.5:1, more preferably 3:1 to 2:1.

It is believed that sometimes in reaction (1), anhydride (as in reaction (2)) production may precede or accompany silyl ester formation. If that happens, anhydride may be converted to the silyl ester simply by continuing to heat the mixture. This is illustrated in Example 20.

Reaction (3) may be carried out in the gas or liquid phases. As mentioned above, if done in the liquid phase, it is preferred to have a cocatalyst present. If done in the liquid phase the preferred temperature range is 140° C. to 250° C., more preferably 160° C. to 175° C. If done in the gas phase it is preferred if the temperature is 190° C. to 250° C.

Reaction (3) must be done in the liquid phase if the starting silyl ester is not sufficiently volatile at the process temperatures. This will be more likely to occur if the silyl ester is formed from a polymeric or cyclic siloxane. When done in the liquid phase and run as a batch reaction a typical reaction time is 10 min. to 3 hr.; or the reaction may be run semi-batch (slow addition of the silyl ester to the reactor) over several hours. Agitation is optional. The reaction is most conveniently done in the liquid phase at ambient pressure.

When reaction (3) is done in the gas phase typical contact times at elevated temperature are 10 sec. to 10 min., usually about 1 to 2 min. The reaction can be run at any convenient pressure, for example 1 Pa to $5 \times 10^5$ Pa, preferably at ambient pressure. Lower than ambient pressures are particularly useful for relatively nonvolatile silyl esters. It is preferred to have the catalyst for this process dispersed onto a solid support such as glass beads. Relatively finely divided catalyst or catalyst precursor is preferred. The weight ratio of catalyst to silyl ester used is not critical, and can range from 10:1 to 0.001:1. Typically it is 0.1:1 to 0.04:1. Preferred catalysts for the gas phase thermolysis are NaF, KF and CsF.

When reaction (3) is done in either the gas or liquid phases, the process should be done under dry and oxygen free conditions to avoid unnecessary decomposition of the starting materials and/or products. It is convenient to carry out the reaction under an inert gas such as nitrogen. The products of the reaction are typically purified by distillation.

One of the products of reaction (3) is a fluorosilane. This can be converted back to siloxane for further use in the process or for other uses. This is done according to reaction (4):

$$\equiv SiF + M(OH)_y \rightarrow \equiv SiOSi\equiv + MF_y \quad (4)$$

where y is the charge on the M cation. The metal hydroxide or an equivalent of the metal hydroxide, such as the metal or metal oxide which can react with water to form the hydroxide. The conversion of the fluorosilane to a tractable siloxane is more difficult when there are 3 fluorine atoms on any single silicon atom, since such compounds tend to form insoluble resins. The reaction is carried out in the presence of water, and the hydroxide is either dissolved in, or slurried with, the water. Preferred metal hydroxides are the alkali hydroxides, and sodium, potassium hydroxides are especially preferred. Basic metal salts are contemplated equivalents of metal hydroxides. Alkaline earth fluorides, such as calcium fluoride, can best be made by reaction of the initially formed metal fluoride with CaO or Ca(OH)$_2$ (see Example 38). Siloxanes containing only one siloxane group are directly formed, but if cyclic or linear polymeric siloxanes are desired, further processing to obtain these as "pure" compounds may be necessary (see V. Bazant et al., supra). Thus it is preferred if the starting fluorosilane is a trihydrocarbylfluorosilane, more preferred if it is a trialkylfluorosilane in which each of the alkyl groups independently has 1 to 4 carbon atoms, and especially preferred if it is trimethylfluorosilane or dimethylethylfluorosilane.

Reaction (4) is conveniently carried out at 0° C. to 100° C., preferably about 10° C. to 60° C. The reaction typically requires about 3–6 hr. at higher temperatures. The reaction is typically two phases, the organic and aqueous phases. These may be separated after the reaction, and the organic phase distilled to recover relatively volatile siloxanes. The pH of the aqueous layer is preferably maintained at about 7 or more throughout the process. The metal fluoride may be recovered by filtration if it is insoluble in water, or the water may be evaporated to recover soluble fluorides. The fluoride content of the metal fluoride may be recovered as HF by treating with strong acids. Substantial amounts of CO$_2$ should be excluded from reaction (4).

In reaction (4), the initial ratio of hydroxyl groups of the metal hydroxide to the total number of fluorines attached to silicon is preferably about 1:1, more preferably about 1.00:1 to 1.05:1. Larger excesses of strong inorganic bases may lead to silanolate formation and/or foaming, both of which are undesirable. This ensures that relatively pure products will be produced. It is preferred to use relatively high concentrations of the metal hydroxide, for example a 10–15% by weight solution of KOH, to keep the volume of the reaction low. If the fluorosilane is relatively low boiling, it may be necessary to do the reaction at higher than atmospheric pressure (trimethylfluorosilane boils at 18° C.).

The trifluorovinyl ethers produced by reaction (3) are useful as monomers in free radical copolymerizations. The copolymers produced are useful as heat and chemically resistant plastics and elastomers, see for example H. Mark., et al., Ed., Encyclopedia of Polymer Science, John Wiley & Sons, New York, vol. 7, 1987, p. 257–269 and vol. 16, 1989, p 614–626, which are hereby included by reference. These references also give details of the known procedures for free radically copolymerizing trifluorovinyl ethers. Tetrafluoroethylene is a preferred comonomer.

Tetrafluoroethylene and perfluoropropyl vinyl ether are copolymerized in aqueous . . . or nonaqueous media . . .

In aqueous copolymerization, water soluble initiators and a perfluorinated emulsifying agent are used. The tetrafluoroethylene is added continuously to the vinyl ether. Molecular weight and molecular weight distribution are controlled by a chain transfer agent. Sometimes a second phase is added to the reaction medium to improve the distribution of the vinyl ether in the polymer . . . ; a buffer is also added.

In nonaqueous copolymerization, fluorinated acyl peroxides are used as initiators that are soluble in the medium . . . ; a chain transfer agent may be added for molecular weight control.

Temperatures range from 15° to 95° C., and the pressures from 0.45 to 3.55 MPa. The temperatures used for the aqueous process are higher than those for the nonaqueous process.

Alkyl vinyl ethers tend to rearrange when exposed to free radicals . . . This could initiate a chain reaction that would result in incomplete rearrangement to the isomeric acid fluoride. Temperatures must be kept low enough to prevent termination by free-radical coupling. In the aqueous process, temperatures below 80° C. minimize the number of acid end groups derived from vinyl ether transfer. In the nonaqueous process, temperature must also be limited to avoid excessive vinyl ether transfer as well as reaction with the solvent. End groups are stabilized by treating the polymer with methanol or ammonia . . .

The polymer is separated from the medium and converted to useful forms such as melt-extruded cubes for melt processible applications.

In the below Examples and Experiments, the following abbreviations and names are used:
Carbowax ® 1000 (Trademark, Union Carbide Corp.)—polyethylene glycol of 1000 molecular weight
glyme—1,2-dimethoxyethane
$(HFPO)_2$-acid fluoride—$CF_3CF_2CF_2OCF(CF_3)COF$
Me—methyl ($—CH_3$)
Mn—number average molecular weight
3-n rbf—3-necked round bottom flask
PPVE—perfluoro(propyl vinyl ether)
PSEPVE—$FSO_2CF_2CF_2OCF(CF_3)CF_2OCF=CF_2$
TAS—tris(dimethyamino)sulfonium
THF—tetrahydrofuran
TMS—trimethylsilyl
TMSF—trimethylfluorosilane
TosOH—p-toluenesulfonic acid It is to be understood that there is no intention to limit the invention to the below examples but the right is reserved to all changes coming within the scope of the claims.

A mixture of $CF_3CF_2CF_2OCF(CF_3)COF$ (16.6 g, 50 mmol) and hexamethyldisiloxane (8.1 g, 50 mmol) was treated with potassium trimethylsilanolate (300 mg). After the minor exotherm subsided, the mixture was heated in an oil bath at 75° C. for 3 hr. $^{19}F$ NMR showed (THF-$d_8$): $-79.6$ and $-85.9$ (AB pattern, $OCF_2$), $-81.37$ (t, J=9, $CF_3$), $-82.25$ (s, $CF_3$), $-129.7$ (s, $CF_2$), $-130.2$ (d, CF), $-157.5$ ($Me_3SiF$). $^1H$ NMR 0.37 ($SiCH_3$). Spectra are in accord with the TMS ester.

The crude ester was treated with 130 mg 18 crown-6, heated to reflux to remove remaining trimethylfluorosilane, cooled, and transferred to a dropping funnel. The mixture was added dropwise to a 3-n rbf maintained at 195° C. A slow $N_2$ purge (ca. 30 mL/min) was used to carry volatile products to a collecting trap at $-78°$ C. There was obtained 12.6 g of colorless liquid consisting of PPVE (34%), $C_3F_7OCHFCF_3$ (17%), and TMSF (49%) (all mole percents).

A sample of potassium trimethylsilanolate (0.5 g, 3.9 mmol) was treated with hexamethyldisiloxane (16.2 g, 100 mmol) and $CF_3CF_2CF_2OCF(CF_3)COF$ (34.2 g, 100 mmol). After the minor exotherm subsided, the mixture was heated in an oil bath at 60° C. for 1 hr, 75° C. for 2.5 hr, and 85° C. for 1 hr. The portion remaining in the reaction vessel was distilled to give a forerun (2.13 g; 18 weight % TMSF, 68% siloxane, 5% TMS ester) and 30.3 g of colorless liquid with bp 139°–140°. $^{19}F$ NMR (THF-$d_8$): $-79.41$ and $-86.15$ (AB pattern, J=152, $OCF_2$), $-81.35$ (t, J=7.1, $CF_3$), $-82.22$ (s, $CF_3$), $-129.69$ (s, $CF_2$), $-130.35$ (d, J=19, CF). An additional 4.0 g of TMS ester product was obtained by vacuum transfer (at 0.1 mm). There remained 1.43 g of white solid, identified as $CF_3CF_2CF_2OCF(CF_3)CO_2K$. $^{19}F$ NMR (THF-$d_8$): $-81.39$ and $-84.18$ (AB pattern, J=164, $OCF_2$), $-81.36$ (t, J=6.9, $CF_3$), $-82.21$ (s, $CF_3$), $-126.4$ (brd s, CF), $-129.86$ (s, $CF_2$).

EXAMPLE 3

The procedure of Example 2 was repeated using potassium trimethylsilanolate (1.5 g, 12 mmol), hexamethyldisiloxane (80.8 g, 499 mmol), and $CF_3CF_2CF_2OCF(CF_3)COF$ (165.5 g, 499 mmol). Thermal program was similar, except temperature was maintained at 85° C. for 2 hr, and 111° C. for 1 hr. Distillation at ca 35 mm pressure afforded 178.5 g, bp 54°–55° C. A minor amount of product appeared in the forerun, and the remaining $CF_3CF_2CF_2OCF(CF_3)CO_2K$ was also coated with ester product.

EXAMPLE 4

A sample of potassium $(HFPO)_2$ acid salt obtained from Example 3 was treated with hexamethyldisiloxane (40.0 g, 247 mmol) and $CF_3CF_2CF_2OCF(CF_3)COF$ (82 g, 247 mmol). The resulting mixture was heated in stages, starting at 60° C. and increasing over 4 hr to 160° C. (bath temperature) while low-boiling by-product was collected in a gas trap. Distillation at 25–45 mm gave 88.2 g of product which was redistilled at atmospheric pressure to give 87.3 g of $CF_3CF_2CF_2OCF(CF_3)CO_2SiMe_3$.

EXAMPLE 5

A sample of [$CF_3CF_2CF_2OCF(CF_3)CO]_2O$ (5.84 g, 9.1 mmol) was treated with hexamethyldisiloxane (1.47 g, 9.1 mmol) and heated at 100° C. for 48 hr. Although the reaction was rather slow, GC analysis showed that conversion of the anhydride to TMS ester was substantially complete (>90%) after this heating period.

EXAMPLE 6

A dry 3-n rbf was charged with diphenyl sulfone (0.20 g, 1.0 mmol) and heated at 180° C. under a slow nitrogen purge for 15 min. The reactor was cooled and charged with $CF_3CF_2CF_2OCF(CF_3)CO_2K$ (184 mg, 0.5 mmol) and $CF_3CF_2CF_2OCF(CF_3)CO_2SiMe_3$ (4.02 g, 10.0 mmol). The mixture was heated in a bath at 160° C. for 1.5 hr during which time 2.0 g of volatile products were collected in a gas trap. $^{19}F$ NMR analysis showed as major constituents (and wt % composition): PPVE (70%), $C_3F_7OCHFCF_3$ (9.8%), TMSF (20%).

EXAMPLE 7

A dry 3-n rbf was charged with cesium fluoride (75 mg, 0.5 mmol) and $CF_3CF_2CF_2OCF(CF_3)CO_2SiMe_3$ (4.02 g, 10 mmol) and heated in an oil bath at 160° C. No observable volatiles were collected after 45 min. the reaction mixture was cooled and treated with 1,3-dimethyl-3,4,5,6-tetrahydro-2(1H)-pyrimidinone (130 mg, 1.0 mmol). The mixture was heated in a bath at 160° C. to consist of PPVE (41.2 mole %), TMSF (54.9%), $C_3F_7OCHFCF_3$ (3.9%), and minor unidentified impurities.

EXAMPLE 8

A reactor for gas phase thermolyses was prepared as follows. A glass U-tube (1.5 cm diameter×18 cm height) was fitted at one end with an addition port and optional supplementary inert gas supply line. The other end of the U-tube was fitted with a ball-joint adapter leading to a series of gas trap collectors. Catalysts and solid supports were added to the reactor under inert atmosphere, and prior to use, the system was purged of adventitious water by heating at 225°-250° C. under a continuous stream of nitrogen.

The above reactor was charged with a mixture of spray-dried potassium fluoride (6 g) and glass spheres (2-3 diameter, 35 mL) and heated in a bath at 225° C. $CF_3CF_2CF_2OCF(CF_3)CO_2SiMe_3$ (1.0 mL) was added dropwise using a supplementary nitrogen carier flow of 30 mL/min. There was collected 0.75 mL (at −78° C.) of colorless liquid. $^{19}F$ NMR and GC analysis showed a ca. 94% conversion of the TMS-ester to a mixture of PPVE and TMSF. Only trace amounts of other components were present. The most prominent of these was $C_3F_7OCHFCF_3$ (<1 mole %).

EXAMPLE 9

Example 8 was repeated using the same reactor and catalyst/support charge. $CF_3CF_2CF_2OCF(CF_3)CO_2SiMe_3$ (16.20 g, 40.3 mmol) was added dropwise over 1.5 hr. There was obtained 13.94 g of liquid product consisting of an equimolar mixture of PPVE and TMSF. Less than 0.2% starting TMS ester remained, and less than 1% $C_3F_7OCHFCF_3$ was produced.

EXAMPLE 10

Example 8 was repeated using the same reactor and catalyst/support charge. $CF_3CF_2CF_2OCF(CF_3)CO_2SiMe_3$ (128.6 g, 0.320 mmol) was added dropwise at ca. 20 g/hr using $N_2$ carrier flow of 34 mL/min. There was obtained 109.1 g of liquid product consisting of PPVE (49.4 mole %), TMSF (48.4%) and $C_3F_7OCHFCF_3$ (2.2%). Distillation using a 24" spinning band column gave 23.9 g of an azeotrope (74/26 TMSF/PPVE by weight), 23.5 g of intermediate fractions, and 51.6 g of >99.8% purity PPVE.

EXAMPLE 11

A sample of $CH_3O_2CCF_2CF_2OCF(CF_3)CF_2OCF(CF_3)COF$ (52.25 g, 107 mmol) was treated with hexamethyldisiloxane (17.7 g, 109 mmol) and the resulting solution was treated with potassium trimethylsilanolate (0.5 g, 3.9 mmol). After the initial exotherm subsided, the mixture was heated in stages to 80° C. at which temperature most of the expected TMSF was collected in a trap. The temperature was increased to 100° C. for 0.5 hr and then 125° C. for 40 min to increase conversion to products. Distillation (0.1 mm) afforded 53.7 g of colorless liquid, bp 63° C. $^{19}F$ NMR (THF-$d_8$/F11): −79.0 and −84.1 (overlapping AB patterns, J=141, $OCF_2$), −79.91 (m, $CF_3$), −82.13 and −82.16 (singlets, $CF_3$'s for two diastereomers), −82.9 (m, $OCF_2$), −121.17 and −121.24 (equally intense triplets, J=2.9, $CF_2$, −130.05 (apparent t, J=18, CF), −144.9 (t, J=22, CF). $^1H$ NMR 3.93 (s, $OCH_3$), 0.39 (s, $SiCH_3$).

EXAMPLE 12

Gas phase thermolysis was carried out using a reactor containing spray-dried KF and glass beads (described in Example 8) modified to accommodate a glass side-arm and distillation flask on the feed side. The U-tube reactor was maintained at 225°-230° C. during the reaction. A sample of $MeO_2CCF_2CF_2OCF(CF_3)CF_2OCF(CF_3)CO_2SiMe_3$ (4.6 g, 8.4 mmol) was slowly added from the distillation flask by reducing the pressure to 0.05 mm and heating the flask in a separate bath at ca. 70° C. Products were collected in a gas trap cooled at −78° C. There was obtained 2.66 g of colorless liquid consisting of a mixture of $Me_3SiF$ and $CF_2=CFOCF_2CF(CF_3)OCF_2CF_2CO_2Me$ as shown by comparison with authentic samples (GC) and $^{19}F$ NMR (THF-$d_8$/F$_{11}$): −79.9 (m, $CF_3$), −82.9 and −84.6 (centers of $OCF_2$ m's), −113.7 (dd, J=65, 85, CF), −121.3 (m, $CF_2$), −121.7 (dd of t's, J=85, 112, 6, CF), −136.65 (dd of t's, J=65, 112, 6, CF), −144.9 (t, J=21.6, CF), −157.5 (m, SiF).

EXAMPLE 13

A sample of $FSO2CF_2CF_2OCF(CF_3)COF$ (35.2 g, 101 mmol) was treated with hexamethyldisiloxane (16.4 g, 101 mmol) and potassium trimethylsilanolate (0.38 g, 3 mmol) at 25° C. The mixture was heated in stages from 50° C. to 97° C., and the temperature was maintained at 97° C. for 1.5 hr. Distillation at 0.2 mm gave a small forerun and 35.2 g of colorless oil with bp =28° C. $^{19}F$ NMR (THF-$d_8$): +45.30 (apparent pentet, J=5.7, $FSO_2$), −81.92 (s, $CF_3$), −77.24 and −83.59 (AB pattern, J=147, with lower-field portion exhibiting additional J=18.5), −112.08 (s, $CF_2$), −130.16 (d, J=18.2, CF), in accord with $FSO_2CF_2CF_2OCF(CF_3)CO_2SiMe_3$.

EXAMPLE 14

A mixture of $FSO2CF_2CF_2OCF(CF_3)CF_2OCF(CF_3)COF$ (7.14 g, 13.9 mmol) and hexamethyldisiloxane (2.26 g, 13.9 mmol) was treated with potassium trimethylsilanolate (64 mg, 0.5 mmol) and heated at 60° C. for 0.5 hr, 80° C. for 0.5 hr, and 125° C. for 1.5 hr. Distillation at 0.05 mm gave a forerun (0.8 g) and the major fraction (4.9 g) at 42°-43° C. Some of the desired product remained in the distillation pot along with the corresponding potassium carboxylate. $^{19}$F NMR (THF-d$_8$): +45.4 (m, FSO$_2$), −77.8 to −80.0 (overlapping lowerfield OCF$_2$ AB and CF$_3$), −82.11 and −82.15 (singlets, CF$_3$), −84.0 (high-field portion of AB pattern, J=140, OCF$_2$), −111.9 (m, CF$_2$), −130.0 (m, CF), −144.4 (overlapping m's, CF). $^1$H NMR 0.38 (s). Spectra are in accord with FSO$_2$CF$_2$CF$_2$OCF(CF$_3$)CF$_2$OCF(CF$_3$)CO$_2$SiMe$_3$.

EXAMPLE 15

A sample of FSO$_2$CF$_2$CF$_2$OCF(CF$_3$)CF$_2$OCF(CF$_3$)CO$_2$SiMe$_3$ (4.8 g, 8.2 mmol) was added dropwise over 1 hr to the U-tube reactor (described in Example 8) containing KF glass beads at 220°-230° C. There was obtained 4.07 g of colorless liquid consisting of a ca. 1/1 mixture of PSEPVE and TMSF. $^{19}$F NMR (THF-d$_8$): +45.3 (m, FSO$_2$), −79.1 (m, CF$_2$), −79.9 (m, CF$_3$), −84.5 (m, CF$_2$), −112.1 (m, SO$_2$CF$_2$), −113.2 (dd, J=66, 84, CF), −121.41 (dd of t's, J=84, 112, CF), −136.45 (dd of t's, J=66, 112, 6, CF), −157.7 (m, FSiMe$_3$).

EXAMPLE 16

A mixture of CF$_3$CF$_2$CF$_2$OCF(CF$_3$)COF (6.0 g, 18 mmol) and cesium fluoride (200 mg, 1.3 mmol) was treated with hexamethylcyclotrisiloxane (1.5 g, 6.8 mmol). The mixture was then treated with TAS Me$_3$SiF$_2$ (50 mg) and allowed to stand for two days. The mixture was heated in an oil bath at 130°-150° C. to provide 2.2 g of colorless liquid. $^{19}$F NMR analysis showed two major products, PPVE and C$_3$F$_7$OCHFCF$_3$ in a ca. 73/27 ratio.

EXAMPLE 17

A mixture of CF$_3$CF$_2$CF$_2$OCF(CF$_3$)COF (16.6 g, 50 mmol) and hexamethylcyclotrisiloxane (4.1 g, 18.5 mmol) was treated with potassium silanolate (300 mg, 2.3 mmol). After the exotherm subsided, the homogeneous solution was heated to 160° C. (internal temperature) while 3.0 mL of colorless liquid was collected in a gas trap. Bulk of this volatile portion was dimethyldifluorosilane; a minor amount of unreacted (HFPO)$_2$ acid fluoride was also collected. The mixture was cooled to 25° C. and 18-crown-6 (80 mg, 0.3 mmol) was added. The mixture was heated to 150° C., then 175°-180° C., at which temperature 11.2 mL of colorless liquid was collected. $^{19}$F NMR (THF-d$_8$) showed −81.84 (t, J=7.4, CF$_3$), −86.35 (m, CF$_2$O), −114.0 (dd, J=66, 85, vinyl CF), −122.1 (dd of triplets, J=85, 112, 5.7, vinyl CF), −129.96 (s, CF$_2$), −135.94 (dd of triplets, J=66, 112, 5.8, vinyl CF), −147.2 (d of m's, J=51, CHF), consistent with a ca 95/5 ratio of PPVE/C$_3$F$_7$OCHFCF$_3$). Small amounts of fluorineended dimethylsiloxane oligomers (predominantly Me$_2$FSiOSiMe$_2$F) were present, as evidenced by septets at −131.9 and −131.15.

EXAMPLE 18

A 4.04 g sample of trimethylsilyl-terminated dimethylsiloxane polymer (mol. wt.=9430) was treated with potassium fluoride (100 mg), potassium trimethylsilanoate (300 mg), and Carbowax ® 1000 (80 mg) and heated at 125° C. for 15 min. The mixture was cooled to 25° C. and treated with CF$_3$CF$_2$CF$_2$OCF(CF$_3$)COF (17.0 g, 51 mmol). The mixture was heated gradually in an oil bath from 50° C. to ca. 190° C., collecting 10.05 g of volatile products in a gas trap at −78° C. $^{19}$F NMR analysis showed a mixture of PVE (75 mole %), C$_3$F$_7$OCHFCF$_3$ (11%), and (HFPO)$_2$-acid fluoride (5%). There remained 3.00 g of by-product ketone [C$_3$F$_7$OCF(CF$_3$)]$_2$CO in the pot.

EXAMPLE 19

A mixture of CF$_3$CF$_2$CF$_2$OCF(CF$_3$)COF (7.54 g, 22.7 mmol) and hexamethylcyclotrisiloxane (1.68 g, 7.6 mmol) was treated with potassium trimethylsilanolate (80 mg, 0.63 mmol). After the mild exotherm subsided and solid trisiloxane had disappeared, the reaction mixture was stirred for an additional 0.5 hr. Volatiles were transferred under vacuum (0.1 mm) to give 7.45 g of colorless liquid. Storage at −25° C. provided 6.1 g (84% yield) of a lower layer. $^{19}$F NMR (THF-d$_8$) featured two AB patterns −79.80 and −86.15 (J=160), and −79.80 and −86.30 (J=160, OCF$_2$), −81.8 (t) and −81.95 (s, CF$_3$'s), −129.98 (s, CF$_2$), −131.98 (d, J=19.6, CF). IR featured C=O bands at 1868 and 1802 cm$^{-1}$. Spectral data are in accord with the anhydride: [CF$_3$CF$_2$CF$_2$OCF(CF$_3$)CO]$_2$O.

EXAMPLE 20

A mixture of CF$_3$CF$_2$CF$_2$OCF(CF$_3$)COF (15.7 g, 47.3 mmol) and octamethylcyclotetrasiloxane (14.0 g, 47.2 mmol) was treated with potassium trimethylsilanolate (256 mg, 2.0 mmol) and stirred at ambient temperature for 1.2 hr. GC and $^{19}$F NMR analyses of an aliquot showed that starting acid fluoride and the anhydride characterized in Example 19 were the predominant fluorocarbon species present. The mixture was then heated at 75° C., and the temperature was gradually increased to 186° C. over 3 hr. GC analysis showed that acid fluoride and the anhydride had been nearly completely consumed. $^1$H NMR showed SiCH$_3$ signals at 0.404 and 0.396 (characteristic of RfCO$_2$SiMe$_2$) as well as SiCH$_3$ at 0.15-0.09. $^{19}$F NMR was likewise consistent with a mixture of dimethyl(perfluoroalkylcarboxy)-terminated and dimethylfluoro-terminated dimethylsiloxane oligomers. GC/MS analysis of these intermediates in a similar experiment provided good evidence for the formation of intermediate silyl esters. For example, the observed m/z of 538.999878 had the elemental composition of C$_{11}$H$_{15}$O$_5$Si$_3$F$_{12}$ (calc'd.=539.0035726) and is assigned to [C$_3$F$_7$OCF(CF$_3$)CO$_2$SiMe$_2$OSiMe$_2$OSiMe$_2$F—Me]. Similarly, observed m/z=613.005127 had the elemental composition [C$_3$H$_{21}$F$_{12}$O$_6$Si$_4$ (calc'd.=613.0223659) and is assigned to [C$_3$F$_7$OCF(CF$_3$)CO$_2$SiMe$_2$O(SiMe$_2$O)$_2$SiMe$_2$F—Me]. The mixture was cooled to 25° C., and 18-crown-6 (132 mg, 0.5 mmol) was added. Upon heating at 160°-185° C. (bath temperature), 8.5 mL (11.4 g) of colorless volatiles were collected in a gas trap. $^{19}$F NMR analysis showed this to consist of PPVE (80 mole %), C$_3$F$_7$OCHFCF$_3$ (10%), and Me$_2$SiFOSiMe$_2$F (9%). There remained after thermolysis 12.6 g of liquid and a small amount of insoluble material. NMR and GC/MS showed the liquid consisted of dimethylfluoro-terminated dimethylsiloxane oligomers (Me$_2$FSiO(Me$_2$SiO)$_n$SiMe$_2$F, n=0 to 13) along with a small amount of cyclic trimer, tetramer, and pentamer (D$_3$ to D$_5$). For example (n=3), observed m/z=377.067902; calc'd. m/z=377.0723831 for C$_9$H$_{27}$F$_2$O$_4$Si$_5$ (M-CH$_3$).

EXAMPLE 21

Example 20 was repeated using $CF_3CF_2CF_2OCF(CF_3)COF$ (17.2 g, 51.8 mmol), freshly distilled octamethylcyclotetrasiloxane (7.7 g, 26 mmol), and potassium trimethylsilanolate (256 mg, 2.0 mmol). 18-Crown-6 (130 mg) was added after GC analysis showed substantial consumption of the intermediate anhydride. Prior to liberation of PPVE, there was collected 1.11 g of volatiles consisting (mol %) of $Me_2SiF_2$ (52), $C_3F_7OCHFCF_3$ (13), $Me_3SiF$ (14), and $(HFPO)_2$-acid fluoride (21). Thermolysis in the presence of 18-crown-6 gave 12.1 g of condensate consisting (wt %) of PPVE (81), $C_3F_7OCHFCF_3$ (7), $Me_2SiFOSiMe_2F$ (7.6), and $Me_2SiF_2$ (5). Yield of PPVE was thus ca. 75%.

EXAMPLE 22

A 3-n rbf fitted with reflux condenser, internal liquid and vapor temperature sensors, was connected to a gas trap for the collection of lower boiling components. The flask was charged with $CF_3CF_2CF_2OCF(CF_3)COF$ (17.2 g, 52 mmol) and octamethylcyclotetrasiloxane (8.0 g, 27 mmol) and then potassium trimethylsilanolate (256 mg, 2 mmol). After the exotherm subsided, the mixture was heated in stages to 150° C. (internal temperature ca. 135° C.) over a period of 5.5 hr. Collection of volatiles began when the internal temperature reached ca. 70° C., but only 1.8 mL of volatiles was obtained. The major part of this trap liquid was $Me_2SiF_2$, minor components included $(HFPO)_2$-acid fluoride and $C_3F_7OCHFCF_3$. The pot residue was treated with 18-crown-6 (130 mg, 0.5 mmol) and heated at 150° C. There was obtained 12.1 g of liquid in the trap after warming to 15° C. $^{19}F$ NMR showed (mol %) the following species: PPVE (72.0), $C_3F_7OCHFCF_3$ (5.9), $Me_2FSiOSiMe_2F$ (10.6), $Me_2SiF_2$ (11.7). The pot residue was processed to provide 5.8 g of oil shown by NMR and GC/MS to consist of a series of fluorine-terminated dimethylsiloxane oligomers containing from 2 to 14 silicon atoms.

EXAMPLE 23

A 3-n rbf fitted with reflux condenser, internal liquid and vapor temperature sensors, was connected to a gas trap for the collection of lower boiling components. The flask was charged with $CF_3CF_2CF_2OCF(CF_3)COF$ (16.5 g, 9.7 mmol) and octamethylcyclotetrasiloxane (7.4 g, 4.8 mmol) and potassium trimethylsilanolate (256 mg, 2 mmol). After the exotherm subsided, the mixture was heated in stages to 150° C. (internal temperature ca. 135° C.) over a period of 2.5 hr. Collection of volatiles began when the internal temperature reached ca. 70° C., but only 1.25 mL of volatiles was obtained. The major part of this trap liquid was $Me_2SiF_2$, minor components included $(HFPO)_2$-acid fluoride and $C_3F_7OCHFCF_3$. The pot residue was then heated at 150°-200° C. for ca. 7 hr. There was obtained 14.3 g of liquid in the trap. From the weight and composition (determined by GC and NMR) the yield of PPVE was determined as 74%. $C_3F_7OCHFCF_3$ was the most prominent by-product, and the ketone $[C_3F_7OCF(CF_3)]_2CO$ was a minor one. $Me_2FSiOSiMe_2F$ and $Me_2SiF_2$ were the volatile fluorosilanes present in the trap. The pot residue was comparable to previous examples and consisted of a series of fluorine-terminated dimethylsiloxane oligomers containing from 2 to 14 silicon atoms.

EXAMPLE 24

A 3-n rbf fitted with reflux condenser, internal liquid and vapor temperature sensors, was connected to a gas trap for the collection of lower boiling components. The flask was charged with $CF_3CF_2CF_2OCF(CF_3)COF$ (15.3 g, 46 mmol) and cesium fluoride (200 mg, 1.3 mmol). Hexamethylcyclotrisiloxane (3.8 g, 17.1 mmol) was added in one portion. After the solid dissolved and the exotherm subsided, the mixture was heated in stages to 175° C. Collection of volatiles began when the internal temperature reached ca. 120° C. There was obtained 7.5 mL (at −78° C.) of liquid in the trap after ca. 4 hr. Volatile product was fractionated by warming to −50, −30, 0, and then 15° C. to remove trapped $CO_2$ and the bulk of dimethyldifluorosilane. $^{19}F$ NMR of the remaining 7.45 g (5.8 mL) of volatile product showed PPVE, $C_3F_7CHFCF_3$, and $(HFPO)_2$-acid fluoride in a 73/13/13 ratio. Continued thermolysis of the pot residue produced a small amount (1.0 mL, 1.52 g) of additional pyrolysate which was predominantly PPVE by $^{19}F$ NMR analysis.

EXAMPLE 25

A 3-n rbf fitted with reflux condenser, internal liquid and vapor temperature sensors, was connected to a gas trap for the collection of lower boiling components. The flask was charged with $CF_3CF_2CF_2OCF(CF_3)COF$ (16.6 g, 50 mmol) and hexamethylcyclotrisiloxane (4.1 g, 18.5 mmol) and then potassium trimethylsilanolate (300 mg, 2.3 mmol). After the solid dissolved and the exotherm subsided, the mixture was heated in stages to 180° C. (internal temperature ca. 160° C.) over a period of 1.0 hr. Collection of volatiles began when the internal temperature reached ca. 100° C., but only 3.0 mL of volatiles was obtained. The major part of trap liquid was $Me_2SiF_2$, minor components included $(HFPO)_2$-acid fluoride and $C_3F_7OCHFCF_3$. After standing for 18 hr, the pot residue was treated with 18-crown-6 (80 mg, 0.3 mmol) and heated at 175°-180° C. There was obtained 11.5 mL (at −78° C.) of liquid in the trap after ca. 1 hr. Volatile product was fractionated by warming to −50, −30, 0, and then 15° C. to give 11.2 mL of liquid. $^{19}F$ NMR (THF-$d_8$/$F_{11}$): −81.84 (t, J=7.4, $CF_3$), −86.35 (m, $OCF_2$), −114.00 (dd, J=66, 85, vinyl CF), −122.10 (dd of t's, $J_t$=5.7, $J_d$=85, 112), −129.96 (s, $CF_2$), −135.94 (dd of t's, $J_t$=5.8, $J_d$=66, 112, vinyl CF); minor signals at −130.18, −131.15, and −131.9 due to $FMe_2Si$- fragments; and d of m's at −147.2 characteristic of $C_3F_7OCHFCF_3$. PPVE purity was estimated as about 95%.

EXAMPLE 26

A 3-n rbf fitted with reflux condenser, internal liquid and vapor temperature sensors, was connected to a gas trap for the collection of lower boiling components. The flask was charged with TMS-terminated polydimethylsiloxane (4.04 g, 3.82 mL, mol wt. ca. 9400), potassium fluoride (100 mg), potassium trimethylsilanolate (300 mg), and Carbowax® 1000 (80 mg). The mixture was heated at 125° C. for 20 min, cooled to 25° C. and treated with $CF_3CF_2CF_2OCF(CF_3)COF$ (17.0 g, 51 mmol). The mixture was heated gradually and in stages to 190° C. (bath temperature) over a period of 4.0 hr. Collection of volatiles began when the internal temperature reached ca. 70° C. There was obtained 8.5 mL (10.1 g) after warming the volatile fraction to 15° C. $^{19}F$ NMR analysis showed this product consisted of a mixture of PPVE (75%), $C_3F_7OCHFCF_3$) (11%), (HFPO)$_2$ (5%), and a minor quantity of unidentified material. The fluorocarbon fraction (3.0 g) obtained from the pot residue consisted mainly of a mixture of diastereomeric ketones of the structure $[C_3F_7OCF(CF_3)]_2CO$.

EXAMPLE 27

A mixture of $[CF_3CF_2CF_2OCF(CF_3)CO]_2O$ (2.57 g, 4.0 mmol) and hexamethyldisiloxane (648 mg, 4.0 mmol) in a sealed glass vial was heated in a bath at 100° C. The (initially) two-phase mixture was stirred vigorously using a small magnetic stir bar. Composition of the mixture was determined by GC analysis using authentic standards. Approximate composition (anhydride/siloxane/$CF_3CF_2CF_2OCF(CF_3)CO_2SiMe_3$) varied with time as follows:

| 18 hr | 60/30/10 |
|---|---|
| 42 hr | 40/20/36 |
| 96 hr | 25/11/64 |
| 120 hr | 20/8/73 |

EXAMPLE 28

A mixture of $[CF_3CF_2CF_2OCF(CF_3)CO]_2O$ (2.57 g, 4.0 mmol) and hexamethyldisiloxane (648 mg, 4.0 mmol) was treated with $CF_3CF_2CF_2OCF(CF_3)CO_2K$ (29 mg, 0.08 mmol) in a sealed glass vial. The reaction mixture was heated in a bath at 100° C. The (initially) two-phase mixture was stirred vigorously using a small magnetic stir bar. Composition of the mixture was determined by GC analysis using authentic standards. Approximate composition (anhydride/siloxane/$CF_3CF_2CF_2OCF(CF_3)CO_2SiMe_3$) varied with time as follows:

| 3.5 hr | 52/23/25 |
|---|---|
| 18 hr | 31/4/65 |
| 42 hr | 15/2.5/83 |
| 96 hr | 9/0/91 |

EXAMPLE 29

A mixture of $[CF_3CF_2CF_2OCF(CF_3)CO]_2O$ (2.57 g, 4.0 mmol) and hexamethyldisiloxane (648 mg, 4.0 mmol) was treated with Me$_3$SiOK (10 mg, 0.08 mmol) in a sealed glass vial. The reaction mixture was heated in a bath at 100° C. The (initially) two-phase mixture was stirred vigorously using a small magnetic stir bar. Composition of the mixture was determined by GC analysis using authentic standards. Approximate composition (anhydride/siloxane/$CF_3CF_2CF_2OCF(CF_3)CO_2$-SiMe$_3$) varied with time as follows:

| 40 min | 35/18/47 |
|---|---|
| 70 min | 24/18/58 |
| 40 hr | 1.3/1.6/97.0 |
| 94 hr | 0.9/1.4/97.7 |

EXAMPLE 30

A sample of fluorine-ended dimethylsiloxane oligomers (2.00 g, est. Mn=400, 5 mmol) obtained from the reaction of (HFPO)$_2$-acid fluoride and octamethylcyclotetrasiloxane was treated with calcium carbonate (0.5 g) and calcium oxide (0.25 g) and heated for 1.5 hr at 150° C., then 0.75 hr at 200° C. without change in composition. The sample was then treated with Ca(OH)$_2$ (0.3 g) and heated at 200° C. for 40 min. GC analysis of the crude mixture showed a low conversion to the cyclic trimer, tetramer (D$_4$), and pentamer (D$_5$) of dimethylsiloxane.

EXAMPLE 31

A sample of fluorine-ended dimethylsiloxane oligomers obtained as in Example 30 (5.0 g) was treated with Ca(OH)$_2$ (0.75 g) and heated at 220° C. for 0.5 hr. The pressure was then reduced to 0.1 mm and 0.45 g of distillate was obtained which consisted mainly of D$_3$, D$_4$, and D$_5$. The mixture was cooled to 25° C. and treated with 75 mg KOH and again heated at 220° C./0.1 mm to provide 2.70 g of a mixture of D$_3$-D$_9$. Structures were confirmed by GC/MS.

EXAMPLE 32

A mixture of fluorine-ended dimethylsiloxane oligomers obtained as in Example 30 (5.24 g), calcium hydroxide (0.9 g), potassium hydroxide (75 mg), and glyme (25 mL) was heated at reflux for 3 hr. Solid was removed by filtration, and the filtrate was treated with water (50 mL). The top layer was dissolved in methylene chloride and washed several times with water, dried, and stripped to give 4.74 g of light yellow oil. Kugelrohr distillation afforded 1.95 g of colorless oil, consisting mainly of D$_4$ and D$_5$ but containing also D$_6$-D$_{12}$. The pot residue was treated with 50 mg KOH and heated under vacuum (150° C., 0.5 mm). The volatiles from this fraction (2.40 g) consisted of D$_3$-D$_7$ with very small amounts of D$_8$ and D$_9$.

EXAMPLE 33

A mixture of fluorine-ended dimethylsiloxane oligomers obtained as in Example 30 (8.12 g, Mn ca. 3000), calcium hydroxide (0.2 g), potassium hydroxide (50 mg), and glyme (35 mL) was heated at reflux for 3 hr. The mixture was filtered, stripped, dissolved in CH$_2$Cl$_2$, washed with water, dried and stripped. The resulting light yellow oil was treated with KOH (25 mg) and heated in an oil bath at 170° C. (0.2 mm) to provide 8.55 g of colorless distillate consisting of 8.00 g of D$_3$-D$_7$ and ca. 0.5 g residual solvent. Yield of cyclic oligomers was thus >98%.

EXAMPLE 34

A glass vial of 20 mL capacity (cleaned by rinsing consecutively with distilled water, acetone, THF; dried at 115° C. for 24 hr and stored in an atmosphere of dry nitrogen) was charged with $CF_3CF_2CF_2OCF(CF_3)COF$ (332 mg, 1.0 mmol) and hexamethyldisiloxane (162 mg, 1.0 mmol) and sealed using a polypropylene screw cap. The vial was heated in a sand bath maintained at 100° C. The reaction was monitored by GC analysis. The vial was cooled to −25° C., then warmed sufficiently to obtain a single liquid phase of reactants and products. After 20 hr under these conditions, two fluorocarbon-containing components were present: $CF_3CF_2CF_2OCF(CF_3)COF$ 44 hr, the composition consisted of acid fluoride (18.6%), anhydride (2.3%), and silyl ester (79.1%).

EXAMPLE 35

A glass vial of 20 mL capacity (cleaned by rinsing consecutively with distilled water, acetone, THF; dried at 115° C. for 24 hr and stored in an atmosphere of dry nitrogen) was charged with $CF_3CF_2CF_2OCF(CF_3)COF$ (498 mg, 1.5 mmol) and 1,1,2,2-tetramethyl-1,3-diethyldisiloxane (285 mg, 1.5 mmol) and a small teflon-coated stir bar and sealed using a polypropylene screw cap. The vial was heated in a sand bath maintained at 100° C. The reaction was monitored by GC analysis. The vial was cooled to $-20°$ C., then warmed sufficiently to obtain a single liquid phase of reactants and products (ca. 0° C.). After 13 hr under these present: $CF_3CF_2CF_2OCF(CF_3)COF$ (83 mole %) and $CF_3CF_2CF_2OCF(CF_3)CO_2SiMe_2Et$ (17%). After 37 hr, the composition consisted of acid fluoride (51.9%), anhydride (2.8%), and silyl ester (45.3%).

EXAMPLE 36

A 3-n rbf was charged with calcium hydroxide (1.59 g, 21.5 mmol), potassium hydroxide (25 mg), and water (30 mL). The mixture was cooled to 0° C. and treated with trimethylfluorosilane (5.0 mL at 0° C., 4.0 g, 43 mmol). After addition was complete, the temperature was allowed to increase to 20° C. The mixture was heated to 50° C., and the reflux condenser was replaced with a still head. Product hexamethyldisiloxane and trimthylsilanol was collected in the lower-boiling fraction which began at ca. 77° C. Separation of the two liquid layers in the distillate provided 2.45 g of organic material which consisted of trimethylsilanol (28%) and hexamethyldisiloxane (68%). Addition of a trace amount of toluenesulfonic acid facilitated the condensation of trimethylsilanol, and resulted in hexamethyldisoloxane of >99% purity. Solid remaining in the distillation pot was filtered and dried to give 1.75 g of white solid.

EXAMPLE 37

A solution of calcium acetate hydrate (16.9 g, 95.9 mmol) in water (50 mL) at 2°–4° C. was treated with trimethylfluorosilane (8.83 g, 96 mmol). The vessel was sealed and allowed to warm to 25° C. over 2 hr. Distillation at atmospheric pressure afforded 6.64 g of colorless liquid which consisted of TMSF (2.5%), TMSOH (2.4%), and $(TMS)_2O$ (95.2%). The pot residue was treated with an antifoaming agent, Dow Corning DB-31, and again subjected to distillation to provide an additional 0.5 g of hexamethyldisiloxane. The remaining solid was filtered and dried to give 5.95 g of material. Elemental analysis confirmed that acetate was present in this product.

EXAMPLE 38

A solution of KOH (86.2 mequiv.) in water (35 mL) was prepared in a 70 mL Fisher-Porter bottle and cooled to 0° C. Trimethylfluorosilane (10.0 mL, 7.93 g) was added, and the vessel was sealed. The mixture was warmed to 25° C. and stirred for 1.75 hr. The vessel was pressurized with $N_2$ (at 7 psi) and heated at 35° C. for 0.5 hr. The mixture was cooled to 0° C. and the top layer was analyzed by GC: 0.1% $H_2O$, 6.6% $Me_3SiOH$, 93.3% $Me_3SiOSiMe_3$. Layers were separated, and the bottom layer was subjected to distillation to remove a small amount of siloxane. Obtained a total of 6.32 g (90.5% recovery) hexamethyldisiloxane after treating the product with a trace of TsOH. The aqueous layer was treated with calcium hydroxide (3.19 g, 43.1 mmol), stirred for 18 hr, and filtered. The basic filtrate was used as reagent for another charge of trimethylfluorosilane as described above. The reaction was monitored by GC. When the composition remained constant (ca. 6% TMSF), an additional charge of KOH (0.335 g) was added and the pressurized mixture was stirred for 18 hr at 45° C. The quantity of isolated hexamethyldisiloxane was 6.11 g.

EXAMPLE 39

A 3-n rbf fitted with a reflux condenser and a $N_2$ purge inlet was charged with diphenyl sulfone (0.6 g, 2.75 mmol). $CF_3CF_2CF_2OCF(CF_3)CO_2SiMe_3$ (4.02 g, 10 mmol) was added in one portion. The mixture was heated in an oil bath at 160° C. There was obtained 1.4 mL (@ 0° C.) after 1.5 hr. $^{19}F$ NMR features PPVE and TMSF as major products, although the PPVE/$C_3F_7OCHFCF_3$ ratio was 65/35. A number of unidentified byproducts were also present.

EXAMPLE 40

A mixture of $CF_3CF_2CF_2OCF(CF_3)CO_2SiMe_3$ (4.0 g), $Cs_2CO_3$ (50 mg), and diphenyl suflone (100 mg) was placed in a 3-n rbf (fitted with a reflux condenser and connected to a gas trap) and heated in an oil bath at 170° C. There was obtained 2.44 g of colorless volatiles which consisted of a 44.4/1.2/54.4 (mol %) mixture of PPVE/$C_3F_7CHFCF_3$/TMSF by $^{19}F$ NMR. GC analysis showed two peaks with an area ratio 67.7/32.3 (PPVE/TMSF).

EXAMPLE 41

Fluorine chemical shifts are reported in ppm from $CFCl_3$. Spectra were recorded on a Nicolet NT200 spectrometer at 188.2 MHz. Solvents with minimum water concentrations are required for reliable results in the NMR experiments described herein. Ether and THF were distilled from sodium-benzophenone and then stored over activated sieves. All reactions were carried out in an atmosphere of dry nitrogen, and manipulations and sample preparations were carried out in a Vacuum Atmospheres drybox. Typical substrate concentrations were ca. 0.1 to 0.2M.

The spectrum of the mixture of $CF_3CF_2CF_2OCF(CF_3)CO_2K$ (92 mg, 0.25 mmol) and $CF_3CF_2CF_2OCF(CF_3)CO_2SiMe_3$ (100 mg, 0.25 mmol) in THF-$d_8$ showed a single set of signals for the fluorocarbon framework: $-80.53$ and $-85.12$ (AB pattern, J=142 Hz, $OCF_2$), $-81.39$ (t, J=7.2 Hz, $CF_3$) $-82.24$ (d, J=1.9 Hz, $CF_3$), $-128.2$ (bd s, CF), $-129.82$ (s, $CF_2$). This spectrum exhibits simple averaged shifts for the corresponding segments of the two components. Spectral parameters for the separate components are given for comparison: [$R_fCO_2K$: $-81.7$ and $-84.0$ (AB pattern), $-81.33$ (t, J=7.2), $-82.2$ (d, J=2.3), $-125.6$ (m, CF), $-129.9$ (s); $R_fCO_2SiMe_3$: $-79.41$ and $-86.18$ (AB pattern, J=152), $-81.37$ (t, J=7.1), $-82.24$ (d, J=1.5), $-129.71$ (s), and $-130.38$ (d, J=18.9); $R_fCO_2$-TAS: $-81.3$ and $-83.2$ (AB pattern, J=146), $-81.22$ (t, J=6.8), $-81.40$ (d, J=1.7), $-122.9$ (m), $-129.76$ (s).]

For simplest analysis in other reactions reported here, examination of the shift for the CF group is the most informative. The spectrum of a similar mixture, prepared by reaction of the anhydride and one equivalent of potassium trimethyl silanolate, was temperature-invariant to $-80°$ C., demonstrating the facility of the trimethylsilyl exchange process.

Chemical shifts of the CF resonance for representative mixtures of $CF_3CF_2CF_2OCF(CF_3)CO_2SiMe_3$/-desilylation reagent (1.00/0.20 mol ratio) are given in the table below. In all these cases, the "desilyation reagent" is only slightly soluble in THF-$d_8$, but dissolves and reacts upon addition of the TMS ester. Shifts for the $R_fCO_2^-$ are dependent upon counterion.

| desilylation reagent | chem. shift of CF |
| --- | --- |
| $Et_4N^+CN^-$ | −128.8 |
| $CF_3CO_2K$ | −129.4 |
| TAS d-10-camphorsulfinate | −129.04 [TAS = tris(dimethylamino)sulfonium] |

A short discussion of the effects of chemical exchange on NMR spectra may be found in R. K. Harris, "Nuclear Magnetic Resonsance Spectroscopy", Pittman Publishing Inc., 1983, Chap. 5.

What is claimed is:

1. A process for the production of trifluorovinyl ethers, comprising:
    (a) reacting a siloxane with a compound of the formula $R^1[O(C_2F_4)COF]_z$ or a compound of the formula $R^1[O(C_2F_4)C(O)O(O)C(C_2F_2)O]_zR^1$ wherein z is 1 or 2 and $R^1$ is a hydrocarbyl or substituted hydrocarbyl radical having z free valencies, and wherein the substituent is inert under process conditions;
    (b) heating in the presence of a thermolysis catalyst at a temperature of about 140° C. to about 350° C., to produce a trifluorovinyl ether and a fluorosilane, provided that when (b) is done in the gas phase, said thermolysis catalyst is not a diaryl sulfone.

2. The process as recited in claim 1 wherein (a) is done in the presence of a first catalyst which under process conditions is capable of generating a compound which contains a carboxylate anion grouping $-O(C_2F_4)CO_2^-$.

3. The process as recited in claim 1 wherein said compound in step (a) is $R^1[O(C_2F_4)COF]_z$.

4. The process as recited in claim 3 wherein said $R^1$ is substituted with one or more of fluorine, ether, ester, sulfonyl fluoride, chloro, bromo, iodo, nitrile, sulfone, or sulfonate ester.

5. The process as recited in claim 3 when said $R^1$ is alkyl or alkylene.

6. The process as recited in claim 5 wherein all hydrogen atoms in said $R^1$ are replaced by fluorine atoms.

7. The process as recited in claim 6 wherein said $R^1$ is substituted with one or more of ether, ester or sulfonyl fluoride.

8. The process as recited in claim 3 wherein said z is 1 and said $R^1$ is perfluoro-n-alkyl containing 1 to 12 carbon atoms, $-[CF_2CF(CF_3)O]_n(CF_2)_mCO_2CH_3$, or $-[CF_2CF(CF_3)O]_t(CF_2)_mSO_2F$, wherein n is 0 or an integer of 1 to 5, t is an integer of 1 to 5, and m is 2 or 3.

9. The process as recited in claim 1, 2, 3, 4, 5, 6, 7, or 8 wherein said siloxane is hexamethyl-disiloxane, hexamethylcyclotrisiloxane, octamethylcyclotetrasiloxane, 1,3-diethyl-1,1,3,3-tetramethyldisiloxane, or poly(dimethylsiloxane).

10. The process as recited in claim 9 wherein said siloxane is hexamethyldisiloxane.

11. The process as recited in claim 1, 2, 3, 4, 5, 6, 7, or 8 in which said first catalyst is a silanolate, fluoride or carboxylate.

12. The process as recited in claim 11 wherein said first catalyst is a potassium silanolate or a potassium carboxylate.

13. The process as recited in claim 1, 2, 3, 4, 5, 6, 7, or 8 in which said thermolysis catalyst is an alkali metal fluoride.

14. The process as recited in claim 13 wherein said thermolysis catalyst is potassium fluoride.

15. The process as recited in claim 1, 2, 3, 4, 5, 6, 7, or 8 in which said heating is carried out in the gas phase and in which said temperature is 190° C. to 250° C.

16. The process as recited in claim 1, 2, 3, 4, 5, 6, 7, or 8 comprising the further step of contacting said fluorosilane with a metal hydroxide and water, at 0° C. to 100° C., to form a metal fluoride and a siloxane.

17. The process as recited in claim 16 wherein said metal hydroxide is sodium hydroxide or potassium hydroxide.

18. The process as recited in claim 17 wherein said fluorosilane is trimethylfluorosilane or dimethylethylfluorosilane.

19. The process as recited in claim 1, 2, 3, 4, 5, 6, 7, or 8 which comprises the further step of free radically copolymerizing said trifluorovinyl ether.

20. The process as recited in claim 1, 2, 3, 4, 5, 6, 7, or 8 wherein $(C_2F_4)$ is $-CF(CF_3)-$.

21. The process as recited in claim 1, 2, 3, 4, 5, 6, 7, or 8 wherein said heating is done while in the liquid phase and in the presence of a cocatalyst.

22. The process as recited in claim 21 wherein said cocatalyst is selected from the group consisting of crown ethers, linear polyethers, sulfones, and dialkyl pyrimidones.

* * * * *